US009173248B2

(12) United States Patent
Baker

(10) Patent No.: US 9,173,248 B2
(45) Date of Patent: Oct. 27, 2015

(54) THAWING OVEN

(75) Inventor: Rodney Warren Baker, Westminster, MD (US)

(73) Assignee: Products Support, Inc., Jessup, MD (US)

(*) Notice: Subject to any disclaimer, the term of this patent is extended or adjusted under 35 U.S.C. 154(b) by 645 days.

(21) Appl. No.: 13/047,183

(22) Filed: Mar. 14, 2011

(65) Prior Publication Data

US 2012/0234817 A1 Sep. 20, 2012

(51) Int. Cl.

| | |
|---|---|
| ***H05B 1/00*** | (2006.01) |
| ***H05B 3/00*** | (2006.01) |
| ***H05B 11/00*** | (2006.01) |
| ***G01K 1/16*** | (2006.01) |
| ***G01J 5/00*** | (2006.01) |
| ***G01K 13/00*** | (2006.01) |
| ***A61M 1/00*** | (2006.01) |
| ***G01N 21/00*** | (2006.01) |
| ***A61L 2/04*** | (2006.01) |
| ***H05B 1/02*** | (2006.01) |

(52) U.S. Cl.

CPC ...................................... *H05B 1/025* (2013.01)

(58) Field of Classification Search

CPC ..... A01N 1/00; A01N 1/0242; A01N 1/0263; H05B 1/025

USPC ...................... 422/1, 44, 46, 82.05, 307, 292, 422/294–297, 300–302; 219/209, 710–712, 219/385, 405, 411, 413, 390; 374/149, 120, 374/121; 604/114

See application file for complete search history.

(56) References Cited

U.S. PATENT DOCUMENTS

| | | | | |
|---|---|---|---|---|
| 3,518,393 | A | 6/1970 | Besseling et al. | |
| 4,251,437 | A * | 2/1981 | Rasmussen et al. | 530/383 |
| 4,486,389 | A | 12/1984 | Darnell et al. | |
| 5,147,330 | A | 9/1992 | Kogel | |
| 5,153,403 | A | 10/1992 | Kimura | |

(Continued)

OTHER PUBLICATIONS http://www.greenerpackage.com/corporate_strategy/sara_lee_speaks_three-pronged_green_goals (Hillshire Farm).*

(Continued)

*Primary Examiner* — Tu B Hoang
*Assistant Examiner* — Michael Hoang
(74) *Attorney, Agent, or Firm* — Kenneth P. Waszkiewicz

(57) ABSTRACT

An apparatus and method for thawing a product. The apparatus includes a heating chamber, and an electrical control unit. The heating chamber includes a product chamber that holds a product, at least one heating element, each heating element emitting infrared energy in a direction of the product, and at least one temperature sensor, each temperature sensor measuring a surface temperature of the product. The electrical control unit includes a processor that controls and monitors said at least one heating element, and said at least one temperature sensor to raise a temperature of the product from an initial temperature to a set-point temperature, a connection to each heating element, and a connection to each temperature sensor.

13 Claims, 4 Drawing Sheets

(56) References Cited

U.S. PATENT DOCUMENTS

| | | | | |
|---|---|---|---|---|
| 5,243,833 | A | 9/1993 | Coelho et al. | |
| 5,779,974 | A | 7/1998 | Kuzyk | |
| 6,007,773 | A | 12/1999 | Kuzyk | |
| 6,328,928 | B1 * | 12/2001 | Schroeder et al. | 422/28 |
| 6,717,110 | B2 * | 4/2004 | Van der Meer et al. | 219/386 |
| 6,748,164 | B1 | 6/2004 | Kuzyk | |
| 6,863,864 | B1 * | 3/2005 | Ingemanson | 422/22 |
| 6,979,803 | B1 * | 12/2005 | Webb | 219/405 |
| 7,722,839 | B2 | 5/2010 | Kuzyk | |
| 2003/0082069 | A1 * | 5/2003 | Kuzyk | 422/1 |
| 2005/0163958 | A1 * | 7/2005 | Nakatsugawa | 428/40.1 |
| 2007/0127901 | A1 | 6/2007 | Kuzyk | |
| 2008/0093357 | A1 * | 4/2008 | Norman et al. | 219/521 |
| 2008/0141867 | A1 * | 6/2008 | Cavada et al. | 99/332 |
| 2009/0283517 | A1 * | 11/2009 | Mackay et al. | 219/700 |
| 2011/0116967 | A1 * | 5/2011 | Roy et al. | 422/22 |

OTHER PUBLICATIONS https://butterballblog.wordpress.com/2009/11/05/what-we-learned-at-butterball-university/ (Butterball Turkey).* http://pomaitest.wordpress.com/category/product-review/page/5/ (KulanaPorkBloodSausage).* http://www.greenerpackage.com/corporate__strategy/sara__lee__speaks__three-pronged__green__goals Jul. 29, 2009.* https://butterballblog.wordpress.com/2009/11/05/what-we-learned-at-butterball-university/ Nov. 5, 2009.* http://pomaitest.wordpress.com/category/product-review/page/5/ Jul. 4, 2009.*

* cited by examiner

THAWING OVEN

BACKGROUND OF THE INVENTION

1. Field of the Invention

The present invention relates, in general, to the field of radiant heating devices. In particular, the present invention relates to an apparatus that thaws a product with infrared energy.

2. Description of the Related Art

Health care facilities use medical products, such as plasma, Fresh Frozen Plasma, blood, and the like, at surgery centers and urgent care facilities. It is a common practice to freeze the product in its sealed prepackaged plastic pouches for storage, and thaw it when necessary. The prior art describes a wet-bath heating system for thawing the frozen product. A health care professional places the frozen product into a temperature-controlled water bath to thaw it to a liquid state. After thawing the product, a health care professional removes it from the water bath, and places it in a temperature-controlled area for use anytime during the next twenty-four hour period.

The prior art wet-bath heating system has certain flaws. Since these prior art systems submerge the medical product in the water bath, there is contact between the heating system and the product. This contact provides the potential for system contamination. If the water bath is contaminated with bacteria, even though the plastic pouch provides a barrier against direct contamination of the contents of the pouch, water from the bath may seep into contact with an inlet end of a connector tube for the pouch. Bacteria in or near a connector tube creates the possibility that when the connector tube seal is punctured, the contents may contact the bacteria, thereby contaminating the contents. A prior art method avoids this class of contamination by placing the pouch to be thawed inside another pouch. Unfortunately, this solution may increase the time required to thaw the contents due to the increased thickness of the plastic in the double-walled pouch, and the double-walled pouch configuration may cause the inner pouch to float. Another drawback of the prior art wet-bath heating system is that if pouch ruptures, the water bath is contaminated and must be sanitized before it can be used again.

Infrared radiators (emitters) use electromagnetic radiation to transfer heat from an energy source to an object. The transfer of the heat occurs without the need for any contact between the emitter and the object, or any transfer medium between the emitter and the object. The wavelength of the infrared radiation ranges from 780 nm to 1 mm, with mid-infrared in the range from 780 nm to 1400 nm, medium infrared in the range between 1400 nm and 3000 nm, and far infrared or dark emitters for everything above 3000 nm.

Thus, there is a need for a heating device that utilizes infrared energy to thaw a product, reduces the time to thaw the product, and maintains separation between the heating system and the pouch to reduce the potential for contamination. The present invention addresses this need.

SUMMARY OF THE INVENTION

Aspects of the present invention provide an apparatus and method for thawing a product. The apparatus includes a heating chamber, and an electrical control unit. The heating chamber includes a product chamber that holds a product, at least one heating element, each heating element emitting infrared energy in a direction of the product, and at least one temperature sensor, each temperature sensor measuring a surface temperature of the product. The electrical control unit includes a processor that controls and monitors said at least one heating element, and said at least one temperature sensor to raise a temperature of the product from an initial temperature to a set-point temperature, a connection to each heating element, and a connection to each temperature sensor.

DETAILED DESCRIPTION OF THE INVENTION

Figure 1:
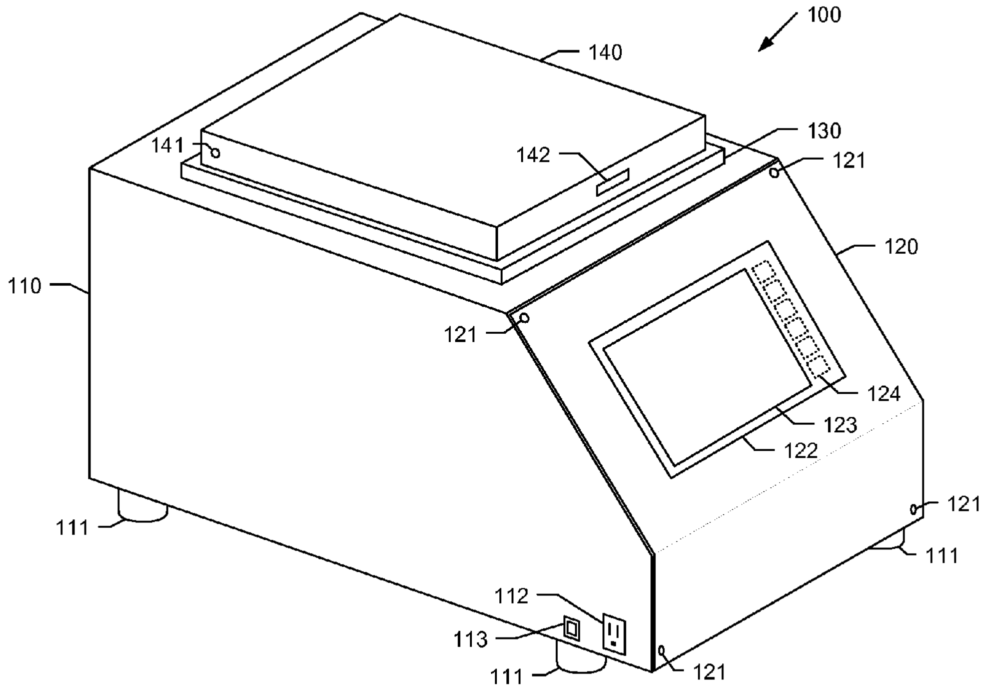
FIG. 1 is a perspective view of one exemplary embodiment of an apparatus in accordance with the present invention.

FIG. 1 is a perspective view of one exemplary embodiment of an apparatus in accordance with the present invention. The thawing unit 100 shown in FIG. 1 is a self-contained apparatus that is capable of thawing a product, such as plasma, Fresh Frozen Plasma, blood, and other biological products, or the like. The thawing unit 100 comprises an enclosure 110, a front cover 120, a chamber door support 130, and a chamber door 140 that enclose a heating chamber and an electrical control unit.

The enclosure 110 is an outer cover that encloses the bottom, three sides, and the top of the thawing unit 100 with a cutout for attaching the chamber door support 130. The enclosure 110 includes leveling feet 111 attached to each of the four corners of the bottom surface of the enclosure 110. The leveling feet 111 function to level the thawing unit 100 before operation. The enclosure 110 also includes a power supply 112, and a data communications port 113. In various embodiments, the power supply 112 receives standard electrical power (120 V AC or 230 V AC), and the data port 113 is an Ethernet data communications port.

The front cover 120 includes fasteners 121 that secure the front cover 120 to the enclosure 110. In one embodiment, the fasteners 121 are thumb screws located at each corner of the front cover 120. The front cover 120 also includes a cutout that receives an operator interface 122 to take input from an operator and allow the operator to control the performance of the necessary functions to thaw the product by allowing the software to hardware communications that will control the thawing unit 100. In one embodiment, the operator interface 122 includes a display 123, and function buttons 124. The display 123 communicates current data and processing messages to an operator, and the function buttons 124 allow the operator to control the processing performed by the thawing unit 100. In one embodiment, the display 123 is a touch screen display that may be programmed to include the function buttons 124.

The chamber door support 130 attaches through a cutout in the top surface of the enclosure 110. The chamber door 140 attaches to the top surface of the chamber door support 130. In one embodiment, two shoulder bolt hinges 141 are the means for attaching the chamber door 140 to the chamber door support 130, thereby allowing the chamber door 140 to rotate 90 degrees from the horizontal top surface of the enclosure 110 and an operator to access to the product chamber 210. The chamber door 140 also includes a handle 142 that allows to the operator of the thawing unit 100 to lift the chamber door 140 and access the heating chamber.

Figure 2:
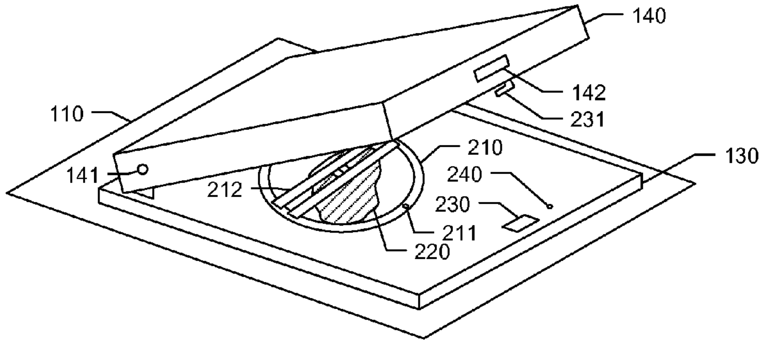
FIG. 2 is another perspective view of the apparatus shown in FIG. 1.

FIG. 2 is another perspective view of the apparatus shown in FIG. 1. As shown in FIG. 2, with reference to FIG. 1, the top surface of the enclosure 110 with the chamber door 140 in a partially open position. The chamber door support 130 includes an opening that receives a product chamber 210. The product chamber 210 includes a locating pin 211 to ensure proper alignment of the product chamber 210 in the heating chamber. A clamp mechanism 212 holds the product 220 in the product chamber 210. In various embodiments, the product 220 is a medical product, such as plasma, Fresh Frozen Plasma, blood, and the like, a biomedical industry product, and a pharmaceutical industry product. The chamber door support 130 also includes an opening 230 that engages a latch 231 in the chamber door 140, and a closed door sensor 240 to detect that the chamber door 140 is properly closed before beginning operation of the thawing unit 100.

Figure 3:
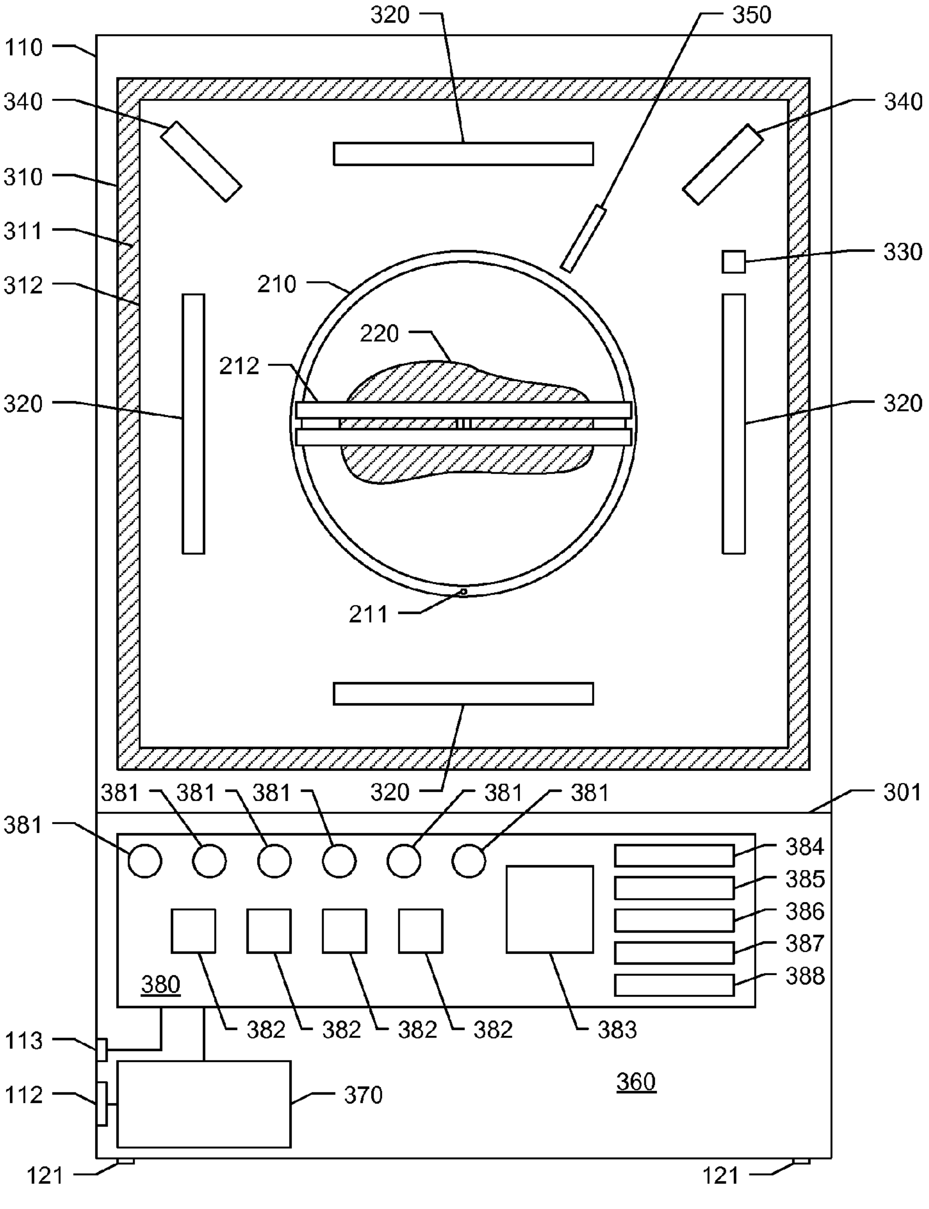
FIG. 3 is a top elevation view, in cross section of the apparatus shown in FIG. 1.

FIG. 3 is a top elevation view, in cross section of the apparatus shown in FIG. 1. As shown in FIG. 3, with reference to FIG. 1 and FIG. 2, the enclosure 110 houses a heating chamber 310 and an electrical control unit 360. In one embodiment, a structural member 301 separates the heating chamber 310 from the electrical control unit 360.

The heating chamber 310 shown in FIG. 3 has an outer wall, an inner wall 312, and a layer of insulation 311. The heating chamber 310 is constructed to enclose an area for the purpose of containing radiated heat and insulating the product 220 held inside the product chamber 210 from the ambient temperature. The heating chamber 310 also includes heating elements 320, thermocouple 330, temperature sensors 340, and a product chamber detection sensor 350.

The heating elements 320 are located inside the heating chamber 310 in the space between the inner wall 312 and the product chamber 210. The heating elements 320 produce a dry, radiant heat that is directed toward the product chamber 210 and the product 220. In one embodiment, the heating elements 320 are ceramic infrared heaters (emitters) that are flat and produce a uniform pattern for even heating at a close proximity between the emitter and the target being heated. In another embodiment, the heating elements 320 are ceramic infrared heaters (emitters) that are concave and produce a concentrated radiant pattern that is highly effective at heating the target. In yet another embodiment, the heating elements 320 are ceramic infrared heaters (emitters) that are convex and produce a distributed radiant pattern that is highly effective at distributing the heat to the target. In one embodiment, the dry, radiant heat that the heating elements 320 emit is mid-infrared energy with a wavelength in the range of 3-50 μm controlled to provide a wavelength of 9.35031 micron or a temperature of 310.15 K. In addition to providing radiant heat, this mid-infrared energy range has also been shown in the prior art to have a therapeutic affect on blood and other medical products. As shown in the embodiment depicted in FIG. 3, the thawing unit 100 positions four heating elements 320 at 90 degree angles around the product chamber 210 to maximize the coverage of the radiated heat exposure on the product 220.

The thermocouple 330 is located inside the heating chamber 310 in the space between the inner wall 312 and the product chamber 210. The thermocouple 330 monitors the actual temperature of one of the heating elements 320 that generates the correct surface temperature of the product 220. In one embodiment, the thermocouple 330 is a type J thermocouple. In another embodiment, the thermocouple 330 is integrated with the heating elements 320 by mounting it in one of the heating elements 320.

The temperature sensors 340 are located inside the heating chamber 310 in the space between the inner wall 312 and the product chamber 210. The temperature sensors 340 are able to measure the surface temperature of the product 220 through the product chamber 210. In one embodiment, the temperature sensors 340 are infrared temperature sensors that can measure the surface temperature of the product 220 through a product chamber 210 that has an acrylic sidewall. The temperature sensors 340 are capable of detecting temperatures in the range of 273.15 K to 388.15 K or wavelengths between 10.61688 and 7.471338 micrometer (μm) with a accuracy of ±276.15 K. A stainless steel housing that encloses the temperature sensors 340 provides an International Protection (IP) Code (i.e., International Protection Rating, or Ingress Protection Rating) of IP67. As shown in the embodiment depicted in FIG. 3, the thawing unit 100 includes two temperature sensors 340 with each positioned around the product chamber 210 and between two adjacent heating elements 320, and separated from each other by 90 degrees to maximize the accuracy of the measurement of the surface temperature of the product 220. In another embodiment, the thawing unit 100 includes two temperature sensors 340 with each positioned around the product chamber 210 and between two adjacent heating elements 320, and separated from each other by 180 degrees to maximize the accuracy of the measurement of the surface temperature of the product 220.

The product chamber detection sensor 350 is located inside the heating chamber 310 in the space between the inner wall 312 and the product chamber 210. The product chamber detection sensor 350 is an inductive proximity sensor that detects metal when it is within 1 mm of the front surface of the product chamber detection sensor 350. A stainless steel housing that encloses the product chamber detection sensor 350 provides a rating of IP67. In one embodiment, the stainless steel housing is a 5 mm threaded stainless steel outer shell. In one embodiment, the product chamber detection sensor 350 is positioned to detect a metal pin that is inserted in the bottom surface of the product chamber 210 when the product chamber 210 is properly oriented in the heating chamber 310.

In one embodiment, the product chamber 210 is located substantially in the center of the heating chamber 310, and is a vessel having a substantially flat bottom surface, and cylindrical side wall that is open at the top. The product chamber 210 functions as a containment system to isolate the product 220 from the heating chamber 310 and the remainder of the enclosure 110. In one embodiment, the product chamber 210 is constructed from an acrylic material having substantial strength, substantial durability, and substantial transparency. The substantial strength of the product chamber 210 prevents a rupture of the product 220 from contaminating the heating chamber 310 and the remainder of the enclosure 110. The substantial durability of the product chamber 210 allows it to withstand irradiation to sanitize it before its initial use, and after a contamination incident. The substantial transparency of the product chamber 210 allows it to filter the passage of the energy from the heating elements 320 thereby allowing a desired range of wavelengths, and preventing an undesired range of wavelengths. In one embodiment, the desired range of wavelengths is mid-infrared energy, and the undesired range of wavelengths above and below mid-infrared energy.

The electrical control unit 360 shown in FIG. 3 includes a power entry module 370, and an electrical control panel 380. The power entry module 370 receives electrical power from the power supply 112 and converts the power for use by the various components of the thawing unit 100. The power entry module 370 and the data communications port 113 connect to the electrical control panel 380.

Figure 4:
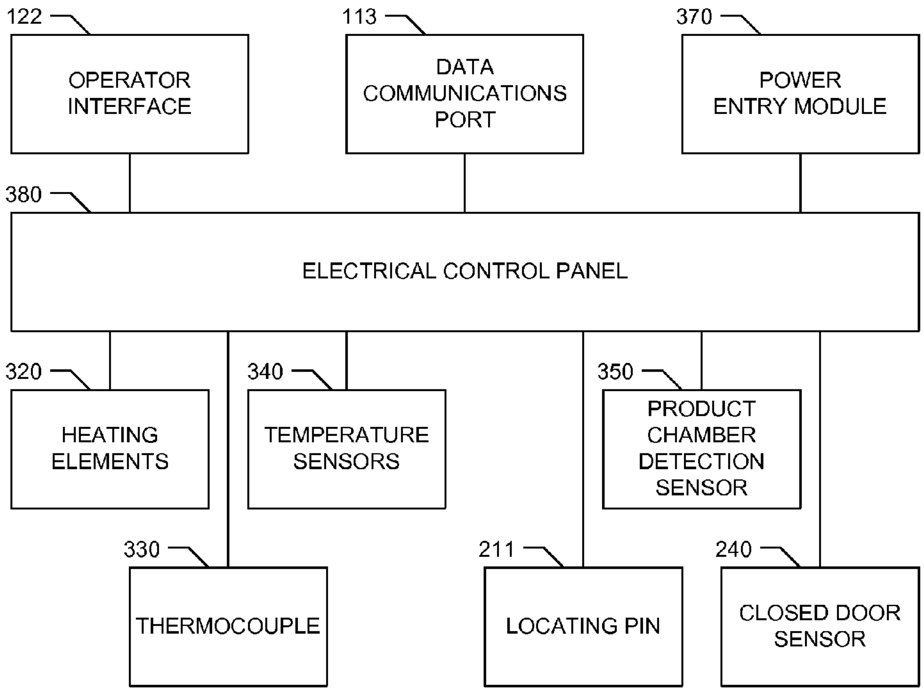
FIG. 4 is a block diagram that illustrates, in detail, one embodiment of the control circuits for the apparatus shown in FIG. 3.

The electrical control panel 380 controls the operation of the hardware components and monitors the performance of the methods of the present invention. In one embodiment, the electrical control panel 380 is a printed circuit board that includes fuses 381 to provide circuit protection for the heating elements 320, relays 382 to control the on-off state of the heating elements 320, a processor 383, a temperature sensor panel connector 384, a safety switch panel connector 385, a heat element feedback panel connector 386, a heat element power panel connector 387, and a terminal block 388. The processor 383 is a special-purpose computing device that performs the methods of the present invention. In one embodiment the processor 383 is a central processing unit (CPU) or application-specific integrated circuit (ASIC) that includes a memory device, and a processor disposed in communication with the memory device, where the processor is configured to execute program instructions to control the hardware components and monitor methods performed by the thawing unit 100. In another embodiment, the processor 383 is an electrically erasable programmable read-only memory (EEPROM) configured to execute program instructions to control the hardware components and monitor methods performed by the thawing unit 100. The processor 383 communicates via the temperature sensor panel connector 384 with the temperature sensors 340 in the heating chamber 310 to monitor the temperature of the product 220 during operation of the thawing unit 100. The processor 383 communicates via the safety switch panel connector 385 with the locating pin 211 and the product chamber detection sensor 350 in the heating chamber 310, and the closed door sensor 240 in the chamber door support 130 to maintain safe operation of the thawing unit 100. The processor 383 communicates via the heat element feedback panel connector 386 and the heat element power panel connector 387 with the heating elements 320 in the heating chamber 310 to monitor the integrity and safety of the heating elements 320. The processor 383 communicates via the terminal block 388 with the operator interface 122 to communicate with the operator of the thawing unit 100. FIG. 4 is a block diagram that illustrates, in detail, one embodiment of the control circuits for the apparatus shown in FIG. 3.

The pre-operation setup of the thawing unit 100 begins with leveling the thawing unit 100 on an operating surface. The operator places a level on the chamber door support 130 and adjusts the leveling feet 111 to level the thawing unit 100 from front-to-back and left-to-right. Once the thawing unit 100 is level, the operator connects a power cord (not shown) to the power supply 112 to provide electrical power to the thawing unit 100, and moves the power switch (not shown) into the "on" position. The operator interface 122 provides step-by-step instructions to the operator of the thawing unit 100.

Figure 5:
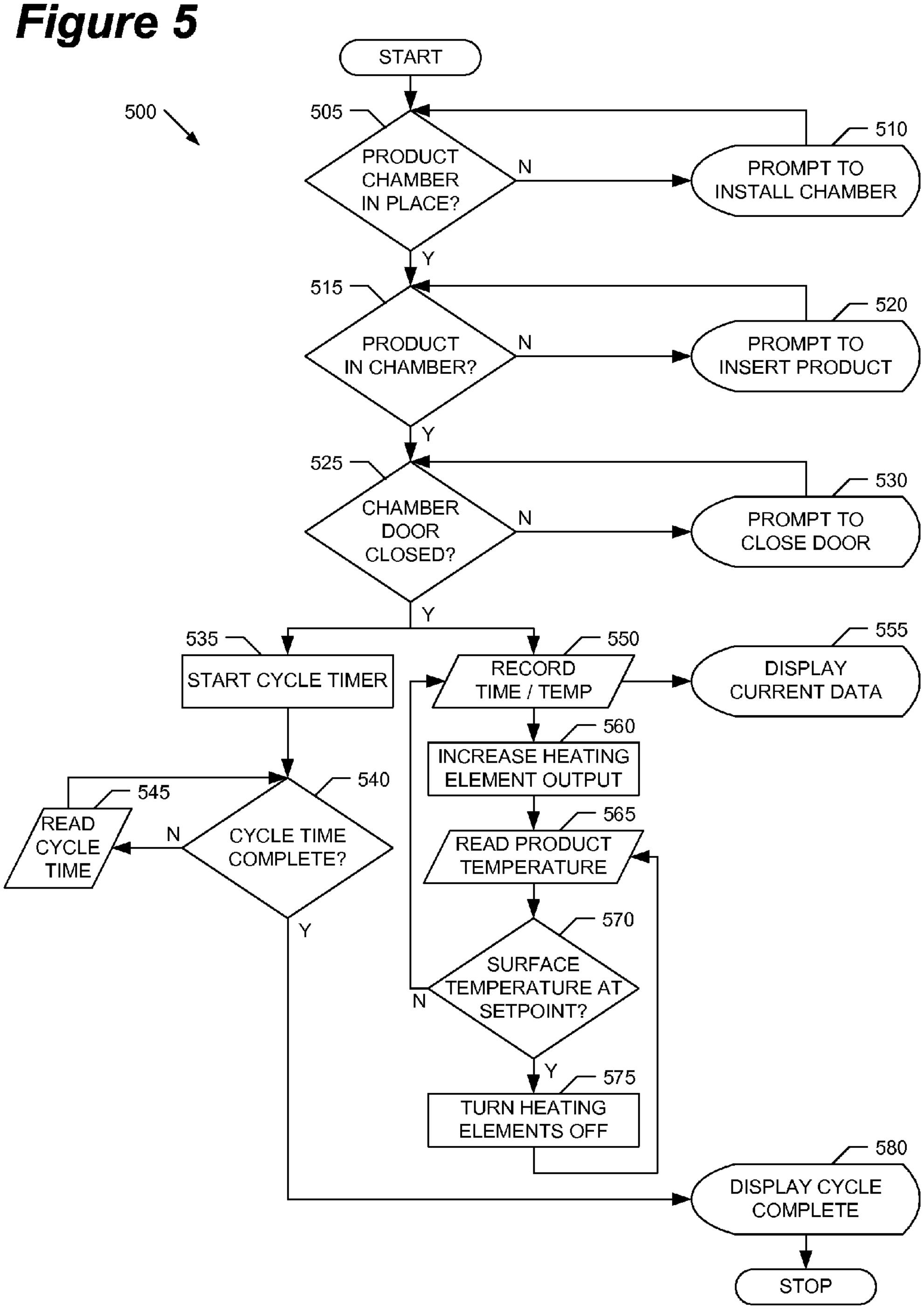
FIG. 5 is a flow diagram that illustrates methods according to various embodiments of the present invention.

FIG. 5 is a flow diagram that illustrates methods according to one embodiment of the present invention. The process 500 shown in FIG. 5 begins with a series of safety checks. The process 500 determines whether the product chamber 210 is in place (step 505). If the product chamber 210 is not in place (step 505, N branch), the operator interface 122 prompts the operator to install the product chamber 210 (step 510) until the product chamber 210 is properly installed. If the product chamber 210 is in place (step 505, Y branch), the process 500 determines whether the product 220 is in the product chamber 210 (step 515). If the product 220 is not in the product chamber 210 (step 515, N branch), the operator interface 122 prompts the operator to install the product 220 (step 520) until it detects the product 220 in the product chamber 210. If the product 220 is in the product chamber 210 (step 515, Y branch), the process 500 determines whether the chamber door 140 is closed (step 525). If the chamber door is not closed (step 525, N branch), the operator interface 122 prompts the operator to close the chamber door 140 until it detects that the chamber door 140 is closed. If the chamber door 140 is closed (step 525, Y branch), the process 500 completes the safety checks and prepares to begin the thawing process.

In one embodiment, the thawing unit 100 will successfully pass the safety checks by the operator opening the chamber door 140, removing the clamp mechanism 212, attaching the product 220 to the clamp mechanism 212, and inserting the clamp mechanism 212 and product 220 into a set of notches in the top of the product chamber 210 until it is fully seated. The operator closes the chamber door 140 until the latch 231 engages the opening 230 in the chamber door support 130. When the closed door sensor 240 detects that the chamber door 140 is closed, and the product chamber detection sensor 350 detects the product 220 and the proper installation of the product chamber 210 in the heating chamber 310, the thawing cycle will begin.

After completing the safety checks, the process 500 begins the thawing process by starting the cycle timer (step 535), and recording the current time and temperature detected by the temperature sensors 340 in the heating chamber 310 (step 550) and displaying the current time and temperature data (step 555) on the operator interface 122. In one embodiment, starting the cycle timer (step 535) and the recording of the current time and temperature (step 550) are started as parallel processes. The process 500 begins heating the product 210 by increasing the temperature output by the heating elements 320 (step 560) and reading the temperature of the product 210 detected by the temperature sensors 340 (step 565). The process 500 determines whether the detected temperature has reached a pre-determined set-point temperature (step 570). If the set-point temperature has not been reached (step 570, N branch), the process records the current time and temperature (step 550), and continues as described above. When the set-point temperature has been reached (step 570, Y branch), the process 500 turns off the power to the heating elements 320 (step 575), reads the temperature of the product 210 detected by the temperature sensors 340 (step 560), and continues as described above. The process 500 continues to read the cycle time (step 545), until it determines that the cycle is complete (step 540, Y branch), and the operator interface 122 displays a "Cycle Complete" message (step 580).

Although the disclosed embodiments describe a fully functioning heating device that utilizes infrared energy to thaw a product, the reader should understand that other equivalent embodiments exist. Since numerous modifications and variations will occur to those reviewing this disclosure, the heating device that utilizes infrared energy to thaw a product is not limited to the exact construction and operation illustrated and disclosed. Accordingly, this disclosure intends all suitable modifications and equivalents to fall within the scope of the claims.

I claim:

1. An apparatus, comprising:

a heating chamber, comprising:

a product chamber that holds a sealed pouch that stores a product, wherein the product chamber includes a locating pin;

at least one heating element, each heating element emitting infrared energy in a direction of the product, wherein said at least one heating element is located outside the product chamber;

at least one temperature sensor, each temperature sensor measuring a surface temperature of the product, wherein said at least one temperature sensor is located outside the product chamber; and a product chamber detection sensor located outside the product chamber; and an electrical control unit, comprising:

a processor that controls and monitors said at least one heating element, and said at least one temperature sensor to raise a temperature of the product from an initial temperature to a set-point temperature;

a connection to each heating element;

a connection to each temperature sensor;

a connection to the product chamber detection sensor; and a connection to the locating pin, wherein the processor monitors the product chamber detection sensor and the locating pin to determine whether the product is present in the product chamber, and whether the product chamber is properly seated in the heating chamber.

2. The apparatus of claim 1, wherein the product is at least one of a medical product, a biomedical product, and a pharmaceutical product.

3. The apparatus of claim 2, wherein the product is at least one of plasma, Fresh Frozen Plasma, and blood.

4. The apparatus of claim 1, wherein the product chamber is a vessel having a flat bottom surface, a cylindrical side wall, and an open top.

5. The apparatus of claim 4, wherein the open top of the cylindrical side wall of the product chamber receives a clamp that holds the sealed pouch that stores the product and suspends the sealed pouch that stores the product within the product chamber to avoid contact between the sealed pouch that stores the product and the product chamber.

6. The apparatus of claim 4, wherein the vessel is an acrylic vessel that filters the infrared energy from said at least one heating element, thereby allowing passage of a desired range of wavelengths, and preventing passage of an undesired range of wavelengths.

7. The apparatus of claim 1, wherein each heating element emits mid-infrared energy.

8. The apparatus of claim 1, wherein each heating element has an emitting surface that is flat, thereby allowing a uniform pattern of the infrared energy in the direction of the product.

9. The apparatus of claim 1, wherein each heating element has an emitting surface that is concave, thereby allowing a concentrated pattern of the infrared energy in the direction of the product.

10. The apparatus of claim 1, wherein each temperature sensor emits an infrared beam to measure the surface temperature of the product.

11. The apparatus of claim 1, wherein said at least one heating element is positioned around the product chamber to maximize the exposure of the infrared energy on the product, and wherein said at least one temperature sensor is positioned around the product chamber to maximize accuracy of the measurement of the surface temperature of the product.

12. The apparatus of claim 1, wherein the heating chamber further comprises:

a chamber door, comprising:

a hinge assembly; and a latch; and a chamber door support, comprising:

an opening that receives the product chamber;

an opening that receives the latch in the chamber door; and a closed door sensor; and wherein the hinge assembly mounts the chamber door on the chamber door support, wherein the chamber door support attaches to a top surface of the heating chamber, wherein the hinge assembly is functional to open the chamber door to allow access to the product chamber, and to close the chamber door to secure the heating chamber, wherein the electrical control unit further comprises a connection to the closed door sensor, and wherein the processor monitors the closed door sensor to determine whether the latch in the chamber door engages the opening in the chamber door support thereby detecting that the chamber door is in a closed position.

13. The apparatus of claim 1, further comprising:

an operator interface, wherein the electrical control unit further comprises a connection to the operator interface, and wherein the processor communicates with the operator interface to start and stop an operation cycle, and to provide a status of the operation cycle.

* * * * *